United States Patent [19]

Brand et al.

[11] Patent Number: 4,536,499
[45] Date of Patent: * Aug. 20, 1985

[54] ISOXAZOLYL INDOLAMINES HAVING ANTI-DIABETIC ACTIVITY

[75] Inventors: Leonard J. Brand, Randolph; Jeffrey Nadelson, Denville, both of N.J.

[73] Assignee: Sandoz, Inc., E. Hanover, N.J.

[*] Notice: The portion of the term of this patent subsequent to Jun. 22, 1999 has been disclaimed.

[21] Appl. No.: 481,373

[22] Filed: Apr. 1, 1983

Related U.S. Application Data

[63] Continuation-in-part of Ser. No. 367,938, Apr. 13, 1982, abandoned.

[51] Int. Cl.³ .................. C07D 413/04; C07D 413/14; A61K 31/40
[52] U.S. Cl. .................................. 514/212; 514/237; 514/252; 514/323; 514/378; 548/247; 548/249; 544/137; 544/367; 546/201
[58] Field of Search ................ 548/247, 249; 544/137, 544/367; 546/201; 424/272, 250, 262, 248.4

[56] References Cited

U.S. PATENT DOCUMENTS

| | | | |
|---|---|---|---|
| 4,336,378 | 6/1982 | Brand et al. | 544/137 |
| 4,336,379 | 6/1982 | Brand et al. | 548/247 |
| 4,336,391 | 6/1982 | Brand et al. | 548/247 |
| 4,397,850 | 8/1983 | Nadelson et al. | 548/247 |
| 4,415,568 | 11/1983 | Brand et al. | 424/248.4 |
| 4,421,752 | 12/1983 | Brand et al. | 548/247 |

Primary Examiner—Donald G. Daus
Assistant Examiner—G. Hendricks
Attorney, Agent, or Firm—Gerald D. Sharkin; Robert S. Honor; Thomas O. McGovern

[57] ABSTRACT

This disclosure describes novel compounds of the formula

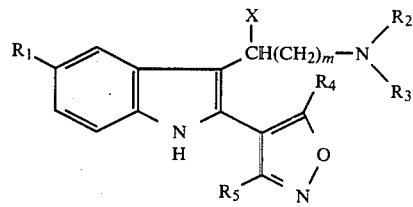

where m is 2, 3 or 4

X is hydrogen or hydroxy $R_1$ represents hydrogen, fluoro, chloro, lower alkyl having 1 to 4 carbon atoms or lower alkoxy having 1 to 4 carbon atoms, and $R_2$ and $R_3$ each independently represent lower alkyl as defined above, or $R_2$ and $R_3$ together with N represent

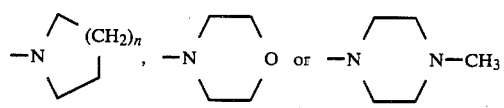

wherein n is 1, 2 or 3, and $R_4$ represents hydrogen or lower alkyl as defined above, and $R_5$ represents hydrogen, lower alkyl, phenyl or phenyl substituted with fluoro, chloro, lower alkyl having 1 to 4 carbon atoms, or lower alkoxy having 1 to 4 carbon atoms, with the proviso that when X is hydroxy, m is 3 or 4, or a pharmaceutically acceptable acid addition salt thereof, which are useful in the treatment of diabetes by inhibiting or impeding post-prandial hyperglycemia.

20 Claims, No Drawings ered using conventional techniques, e.g., evaporation
ISOXAZOLYL INDOLAMINES HAVING ANTI-DIABETIC ACTIVITY This is a continuation in part of U.S. patent application Ser. No. 367,938 filed Apr. 13, 1982 now abandoned.

This invention relates to substituted indolamines which exhibit anti-diabetic activity. In particular, it relates to substituted isoxazolyl indolamines and pharmaceutically acceptable acid addition salts.

The compounds of this invention may be represented by the following structural formula:

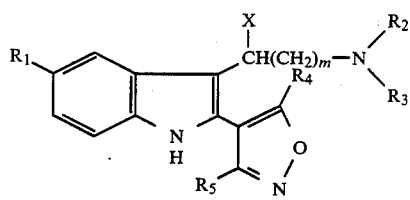

where m is 2, 3 or 4, x is hydrogen or hydroxy, $R_1$ represents hydrogen, fluoro, chloro, lower alkyl, i.e., alkyl having 1 to 4 carbon atoms, e.g., methyl, ethyl, isopropyl and the like, or lower alkoxy, i.e., alkoxy having 1 to 4 carbon atoms, e.g., methoxy, ethoxy, and the like, and $R_2$ and $R_3$ each independently represent lower alkyl as defined above, or $R_2$ and $R_3$ together with N represent

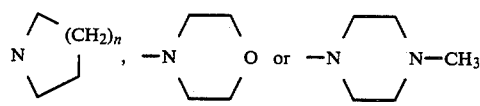

wherein n is 1, 2 or 3, and $R_4$ represents hydrogen or lower alkyl as defined above, and $R_5$ represents hydrogen, lower alkyl as defined above, phenyl or phenyl substituted with fluoro, chloro, lower alkyl as defined above, or lower alkoxy as defined above, with the proviso that when X is hydroxy, m is 3 or 4, or a pharmaceutically acceptable salt thereof.

The compounds of formula (I) in which m is 2 and X is hydrogen are prepared in accordance with the following reaction scheme:

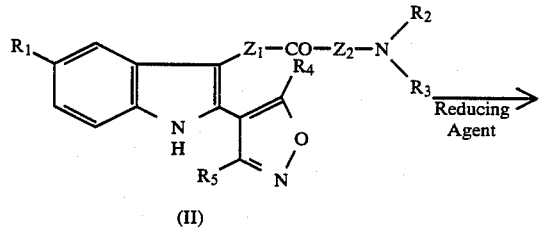

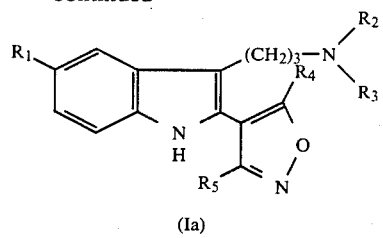

where one of $Z_1$ and $Z_2$ is —CH$_2$CH$_2$— and the other is a direct bond and $R_1$, $R_2$, $R_3$, $R_4$ and $R_5$ are as defined above.

The compounds of formula (Ia) are prepared by reducing a compound of the formula (II) with a reducing agent such as aluminum hydride, sodium bis(2-methoxyethoxy)aluminum hydride, lithium aluminum hydride or diborane, preferably lithium aluminum hydride. In the preferred process, $Z_1$ is a direct bond and $Z_2$ is —CH$_2$CH$_2$—. The reaction is carried out in the presence of an inert organic solvent; and although the particular solvent employed is not critical, the preferred solvents are ethers, such as diethylether, dioxane or tetrahydrofuran, the latter being especially preferred. The temperature of the reaction is also not critical, but it is preferred that the reaction be run at a temperature of from about 0° to 60° C., preferably 20° to 30° C. When $Z_1$ is —CH$_2$CH$_2$— and 40° to 120° C., preferably the reflux temperature of the solvent when $Z_2$ is —CH$_2$CH$_2$—. The reaction is run from about 1 to 12 hours, preferably from about 2 to 5 hours, when $Z_1$ is —CH$_2$CH$_2$— and 30 minutes to 6 hours, preferably 1 to 4 hours when $Z_2$ is —CH$_2$CH$_2$—. The product is recovered using conventional techniques, e.g., evaporation and crystallization.

The compounds of formula (II) in which $Z_1$ is a direct bond and $Z_2$ is —CH$_2$CH$_2$—, are prepared according to the following reaction scheme:

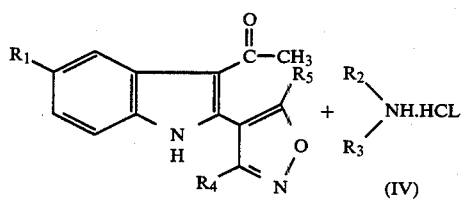

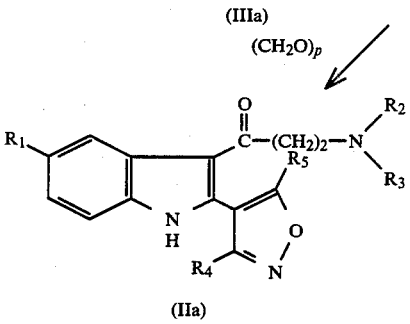

where p is >3, and $R_1$, $R_2$, $R_3$, $R_4$ and $R_5$ are as defined above.

The compounds of formula (IIa) are prepared by treating a compound of the formula (IIIa) with a compound of the formula (IV) in the presence of an excess of paraformaldehyde and an organic solvent. Although the particular solvent employed is not critical, it is preferred that the reaction be run in the presence of the lower alkanols, e.g., methanol, ethanol and the like, preferably ethanol. The temperature of the reaction is not critical but it is preferred that the reaction be run at a temperature of from about 60° to 150° C., preferably the reflux temperature of the solvent. The reaction is run from about 2 to 35 hours, preferably from about 20 to 30 hours. The product may be recovered by conventional techniques, e.g., crystallization.

The compounds of formula (II) in which $Z_1$ is —$CH_2CH_2$— and $Z_2$ is a direct bond are prepared according to the following reaction scheme:

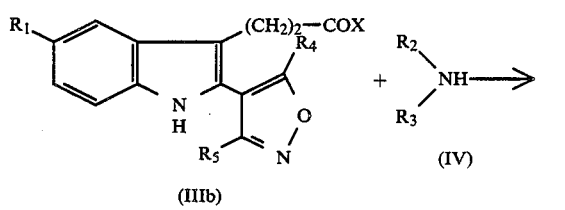
(IIIb)    (IV)

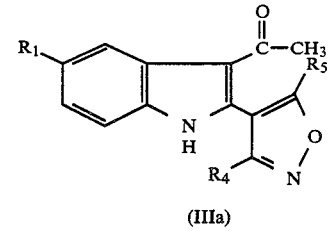
(IIIa)

where X represents chloro or bromo and $R_1$, $R_2$, $R_3$, $R_4$ and $R_5$ are as defined above.

The compounds of formula (IIb) are prepared by treating a compound of the formula (IIIb) with a compound of the formula (IV) in the presence of a solvent. Although the particular solvent employed is not critical, the preferred solvents include water, an excess of a compound the formula (IV), a halogenated hydrocarbon such as methylene chloride, an ether such as diethylether or tetrahydrofuran, preferably a combination of water, methylene chloride and an excess of the compound of formula (IV). The temperature of the reaction is not critical, but it is preferred that the reaction be run from about −10° to 50° C., preferably from about 0° to 30° C. The reaction is run from about 1 to 12 hours, preferably from about 2 to 5 hours. The product is recovered using conventional techniques e.g., crystallization.

The compounds of formula (IIIa) are prepared in accordance with the following reaction scheme:

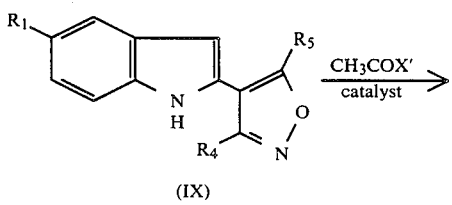
(IX)

where X' is hydroxy, chloro or bromo, and $R_1$, $R_4$ and $R_5$ are as defined above.

The compounds of formula (IIIa) are prepared by reacting a compound of the formulae (IX) in acetonitrile with acetic acid in the presence of phosphoric acid and trifluoroacetic acid anhydride. Alternatively, the compound of formula (IX) can be reacted first with silver trifluoromethanesulfonate and then with an acetylhalide, such as acetylchloride in the presence of an organic solvent. Although the particular solvent employed in the latter procedure is not critical, the preferred solvents include the halogenated hydrocarbons such as methylene chloride, chloroform and the like, preferably methylene chloride. The temperature of the reaction is not critical, but it is preferred that the reaction be run at a temperature of from about 10° to 80° C., preferably 20° to 40° C. for the acetic acid method and about 20° to 45° C., preferably from about 25° to 35° C. for the acetyl halide method. The reaction is run from about 2 to 24 hours for the acetic acid procedure and 2 to 8 hours for the acetyl halide method, preferably from about 3 to 6 hours for both methods. The product may be recovered by conventional techniques, e.g., crystallization.

The compounds of formula (IIIb) are prepared according to the following reaction scheme:

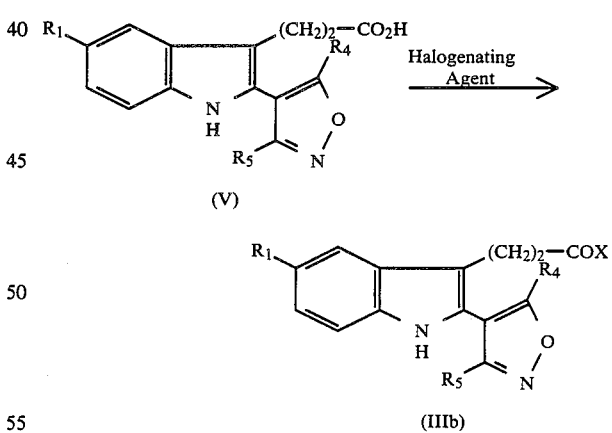
(V)

(IIIb)

where X, $R_1$, $R_4$ and $R_5$ are as defined above.

The compounds of formula (IIIb) are prepared by reacting a compound of the formula (V) with a halogenating agent in the presence of an inert organic solvent. Although the particular halogenating agent is not critical, the preferred halogenating agents include thionyl chloride, thionyl bromide, phosphorous oxychloride and the like, preferably thionyl chloride. The preferred inert organic solvents include the ethers such as diethylether, dioxane or tetrahydrofuran or an aromatic hydrocarbons such as benzene, toluene and the like, preferably tetrahydrofuran. The temperature of the reaction is not critical but it is preferred that the reaction be run at a temperature of from about 0° to 60° C., preferably from about 20° to 30° C. The reaction is run from about 5 to 24 hours, preferably from about 16 to 20 hours. The product may be recovered by conventional techniques, e.g., evaporation.

The compounds of formula (V) are prepared according to the following reaction scheme:

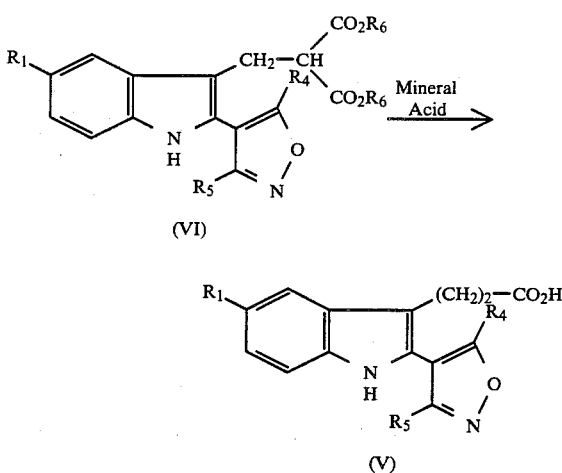

where each $R_6$ independently represents lower alkyl having 1 to 4 carbon atoms and, $R_1$, $R_4$, and $R_5$ are as defined above.

The compounds of formula (V) are prepared by hydrolyzing and decarboxylating a compound of the formula (VI), using an aqueous mineral acid. Suitable acids which can be employed include hydrochloric acid and hydrobromic acid, preferably hydrochloric acid. The temperature of the reaction is not critical, but it is preferred that the reaction be carried out at a temperature of from about 90° to 150° C., preferably at the reflux temperature. The reaction is run from about 48 to 85 hours preferably from 60 to 70 hours. The product may be recovered using conventional techniques e.g., recrystallization.

The compounds of formula (VI) are prepared according to the following reaction scheme:

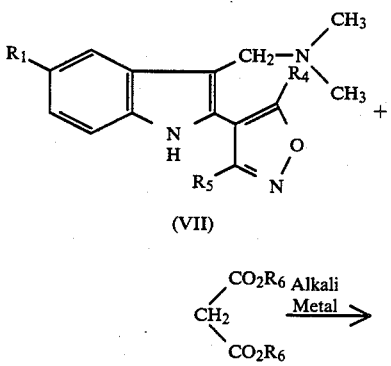

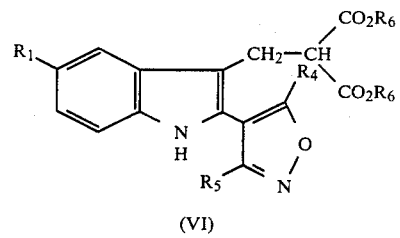

where $R_1$, $R_2$, $R_3$, $R_4$, $R_5$, and $R_6$ are as defined above.

The compounds of formula (VI) are prepared by reacting a compound of the formula (VII) with a compound of the formula (VIII) in the presence of an alkali metal such as sodium, potassium or lithium, preferably sodium. The reaction is carried out in the presence of an excess of a compound of formula (VIII). The temperature of the reaction is not critical, but it is preferred that the reaction be run from about 100° to 200° preferably from about 120° to 150° C. The reaction is run from about 12 to 48 hours preferably from about 20 to 30 hours. The product is recovered using conventional techniques e.g., filtration.

The compounds of formula (VII) are prepared according to the following reaction scheme:

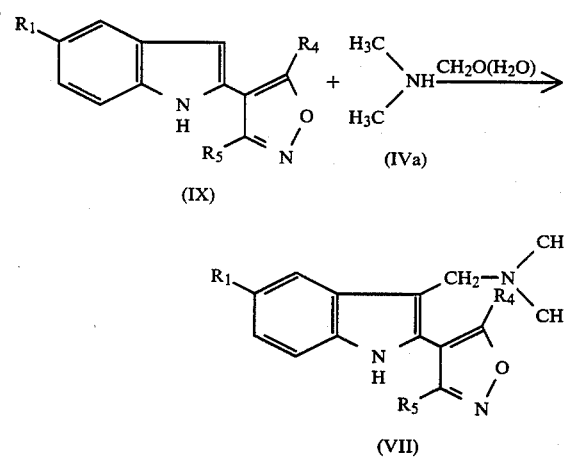

where $R_1$, $R_4$ and $R_5$ are as defined above.

The compounds of formula (VII) are prepared by reacting a compound of the formula (IX) with a compound of the formula (IVa) and a formaldehyde solution in the presence of acetic acid and an organic co-solvent. Although the particular co-solvent employed is not critical, it is preferred that the reaction be run in the presence of an ether such as diethyl ether, tetrahydrofuran or dioxane, the latter being especially preferred. The temperature of the reaction is not critical but it is preferred that the reaction be run at a temperature of from about −10° to 30° C., preferably from about 0° to 10° C. The reaction is run from about 30 minutes to 8 hours, preferably from about 1 to 3 hours. The product is recovered using conventional techniques, e.g., crystallization.

The compounds of formula (I) in which m is 3 or 4 are prepared in accordance with the following reaction scheme:

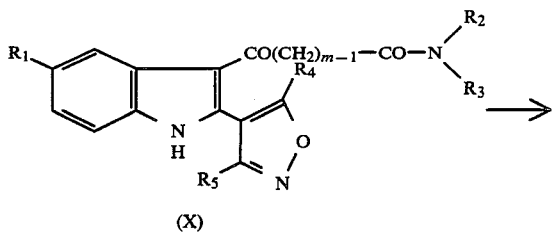

(X)

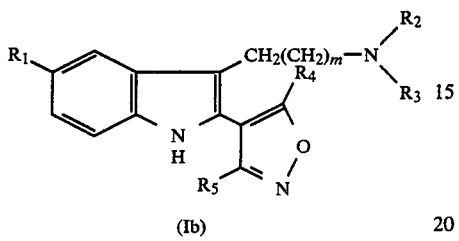

(Ib)

where m, X, $R_1$, $R_2$, $R_3$, $R_4$ and $R_5$ are as defined above.

The compounds of formula (Ib) are prepared by reducing a compound of the formula (X) with a reducing agent, such as sodium bis(2-methoxyethoxy)aluminum hydride, aluminum hydride, lithium aluminum hydride, and the like, preferably lithium aluminum hydride. Whenever the above reducing agents are used, it is preferred that the reaction be run in the presence of an inert atmosphere, e.g., nitrogen, helium or argon, preferably nitrogen. The reaction is carried out in the presence of an inert organic solvent, and although the particular solvent employed is not critical, the preferred solvents are hydrocarbons such as hexane or benzene or ethers, such as diethylether, dioxane or tetrahydrofuran, the latter being especially preferred. The temperature of the reaction is critical. In order to obtain the compounds of formula (Ia) in which X is hydrogen, the reaction is run at a temperature of from about 40° to 150° C., preferaby the reflux temperature of the solvent. To prepare the compounds of formula (Ia) in which X is OH, the reaction is run at a temperature of from about −30° to 30° C., preferably 20° to 35° C. The reaction is run from about 30 minutes to 5 hours, preferably 1 to 3 hours. The product (Ib) is recovered by conventional techniques, for example, evaporation and recrystallization.

The compound of formula (X) may be prepared in accordance with the following reaction scheme:

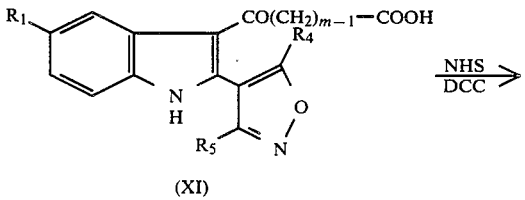

(XI)

Complex + HN$\begin{matrix}R_2\\\\R_3\end{matrix}$ →

(IV)

-continued

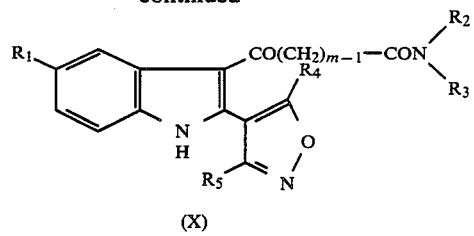

(X)

where
NHS is N-hydroxysuccinimide,
DCC is dicyclohexylcarbodiimide and
m, $R_1$, $R_2$, $R_3$, $R_4$ and $R_5$ are as defined above.

The compounds of formula (X) are prepared by first reacting a compound of formula (XI) with N-hydroxysuccinimide and dicyclohexylcarbodiimide in an inert solvent at a temperature of between 10° C. and 50° C., preferably 20° to 30° C., for 2 to 10 hours, preferably 3 to 7 hours. Although the particular solvent used is not critical, the preferred solvents are hydrocarbons, such as hexane and heptane, aromatic hydrocarbons, such as benzene or toluene, ethers such as diethylether or dioxane and especially chlorinated hydrocarbons such as methylene chloride and the like. The complex solution obtained is then reacted, preferably after filtering, to remove undissolved solids with an aqueous solution of the amine of formula (IV). If desired, additional solvents from those listed above may also be added. The temperature at which the reaction is carried out is not critical, but it is preferred that the second part of the reaction be run between about 10° to 50° C., preferably between about 20° to 30° C. The time of the reaction also is not critical, but it is preferred that the second part of the reaction be run for 2 to 24 hours, especially 6 to 18 hours. The compound of formula (XI) is isolated by conventional techniques, e.g., evaporation and crystallization.

The compound of formula (XI) may be prepared in accordance with the following reaction scheme:

R$_1$—[indole structure]—CO(CH$_2$)$_{m-1}$—COOR$_6$, R$_4$, R$_5$, O, N (XII)

R$_1$—[indole structure]—CO(CH$_2$)$_{m-1}$—COOH, R$_4$, R$_5$, O, N (XI)

where m, $R_1$, $R_4$, $R_5$ and $R_6$ are as defined above.

The compounds of formula (XI) are prepared by hydrolyzing a compound of the formula (XII) with an alkali metal hydroxide, such as sodium hydroxide or potassium hydroxide, in an aqueous alcohol solvent. Although the particular alcohol used is not critical, ethanol and especially methanol are preferred. The temperature at which the reaction is run is also not critical, but it is preferred that the reaction be carried out between about 15° to 80° C., preferably between about 25° to 45° C. The time of the reaction also is not critical, but it is preferred that the reaction be run for 30 minutes to 5 hours, especially 1 to 2 hours. The compound of formula (XI) is isolated by conventional techniques, e.g., evaporation and crystallization.

The compound of formula (XI) may be prepared in accordance with the following reaction scheme:

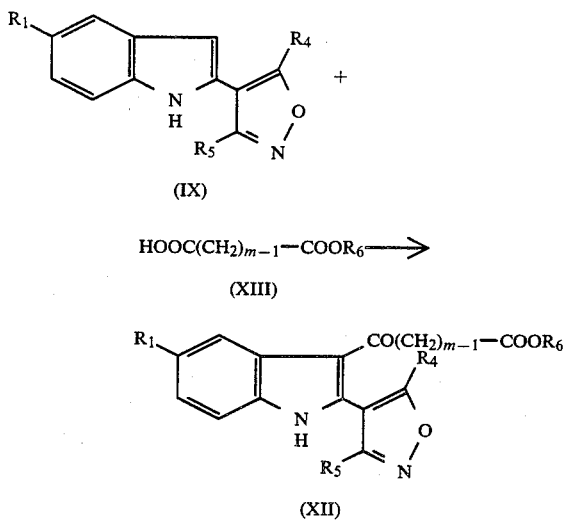

where m, $R_1$, $R_4$, $R_5$ and $R_6$ are as defined above.

The compounds of formula (XII) are prepared by reacting a compound of the formula (IX) in acetonitrile with a compound of formula (XIII) in the presence of phosphoric acid and trifluoroacetic acid anhydride. The temperature of the reaction is not critical, but is is preferred that the reaction be run at a temperature of from about 0° to 70° C., preferably 20° to 35° C. The reaction is run from about 2 to 24 hours, preferably from about 16 to 20 hours. The product may be recovered by conventional techniques, or used in crude form for the preparation of compound (XI) above.

The compounds of formulae (IVa), (VII), (IX) and (XIII) are known and can be prepared by methods described in the literature. The compounds of formula (IX) and their preparation is disclosed in European Application No. 81810131.3. filed Apr. 1, 1981, which published under publication No. 0038298/Al of Oct. 21, 1981 and also in corresponding U.S. patent application Ser. No. 196,784, filed Oct. 14, 1980, which issued as U.S. Pat. No. 4,336,378 on June 22, 1982, Ser. No. 245,188, filed Mar. 18, 1981, which issued as U.S. Pat. No. 4,336,379 on June 22, 1982 and Ser. No. 251,068, filed Apr. 6, 1981, which issued as U.S. Pat. No. 4,336,391 on June 22, 1982.

The compounds of formula (I), and their pharmaceutically acceptable salts, are useful because they exhibit pharmacological activity in animals. In particular, the compounds of formula (I) are useful in the treatment of diabetes by inhibiting or impeding post-prandial hyperglycemia or as a hypoglycemic agent.

The compounds of formula (I) are useful in treatment of diabetes by inhibiting or impeding post-prandial hyperglycemia as indicated by a lowering of the blood sugar levels in male Wistar rats after an oral starch load. In this test male Wistar rats in groups of 5 which are fasted for 16 hours are given an initial dose of from 50 to 200 mg/kg p.o. of the test compound. One hour later the rats are given 1.0 gram per kilogram of animal body weight of cooked starch load. Thirty minutes after administration of the starch, the rats are anesthetized with 120 milligrams per kilogram of animal body weight of sodium hexobarbital after which blood is collected via cardiac puncture. The blood samples are placed in an autoanalyzer cup containing 0.1 milliliters of heparin (1,000 units per milliliters). The heparinized blood is used to determine the blood sugar level with an autoanalyzer. The blood sugar content is compared to the control group which receives 0.5% carboxymethyl cellulose and an oral starch load and are run concurrently. Serum glycose levels are also determined on non-heparinized blood samples using the Technicon autoanalyzer 2-glucose oxidase method.

The compounds of formula (I) are also useful in the treatment of diabetes as hypoglycemic agents as indicated by the lowering of serum glucose in 4 male cebus monkeys weighing 2 to 4 kilograms which are fasted for 16 to 18 hours before testing. At least a three-day interval is allowed between experimental days. The compound to be tested is suspended in 0.5% carboxymethyl cellulose (CMC) for oral dosing. Two blood samples for basal serum glucose level are taken at minus 30 min. and just before administration of placebo (0.5% CMC) or the test compound at 5, 10, 20 and 40 mg/kg of animal body weight. Blood samples are thereafter taken hourly for 6 hours. Serum glucose levels were determined by the Technicon Auto-analyzer 2-glucose oxidase method, and these glucose levels are then compared with the glucose levels of the control group which received orally 0.5% CMC and is run concurrently. To validate this experiment a known hypoglycemic standard is run each time the test is carried out.

For the inhibition of post-prandial hyperglycemia and use as a hypoglycemic agent, the compounds of formula (I) and their non-toxic, pharmaceutically acceptable salts may be administered orally or parenterally as such or admixed with conventional pharmaceutical carriers. They may be administered orally in such forms as tablets, dispersible powders, granules, capsules, syrups and elixirs, and parenterally as solutions, e.g., a sterile injectable aqueous solution. The compositions for oral use may contain one or more conventional adjuvants, such as sweetening agents, flavoring agents, coloring agents and preserving agents, in order to provide an elegant and palatable preparation. Tablets may contain the active ingredient in admixture with conventional pharmaceutically acceptable excipients, e.g., inert diluents, such as calcium carbonate, sodium carbonate, lactose, and talc, granulating and disintegrating agents, e.g., starch and alginic acid, binding agents, e.g., magnesium stearate, stearic acid and talc. The tablets may be coated by known techniques to delay disintegration and absorption in the gastro-intestinal tract and thereby provide a sustained action over a longer period. Similarly, suspensions, syrups and elixirs may contain the active ingredient in admixture with any of the conventional excipients utilized in the preparation of such compositions, e.g., suspending agents such as methylcellulose, tragacanth and sodium alginate; wetting agents such as lecithin, polyoxyethylene stearate and polyoxyethylene sorbitan monooleate; and preserviatives such as ethyl p-hydroxybenzoate. Capsules may contain the active ingredient alone or admixed with an inert solid diluent, e.g., calcium carbonate, calcium phosphate and kaolin. The injectable compositions are formulated as known in the art. These pharmaceutical preparations may contain up to about 90% of the active ingredient in combination with the carrier or adjuvant.

The effective amount of active ingredient for inhibiting post-prandial hyperglycemia employed in the treatment of diabetes may vary depending on the particular compound employed, the mode of administration and the severity of the condition being treated. However, in general, satisfactory results in the treatment of diabetes are obtained when a compound of formula (I), or a pharmaceutically acceptable salt thereof, is administered at a daily dosage of from about 10 milligrams to about 800 milligrams per kilogram of animal body weight, preferably given orally and in divided doses two to four times a day, or in sustained release form. For most large mammals, the total daily dosage is from about 75 milligrams to about 2000 milligrams, preferably given at mealtime as conventional in treatments with substances having such activity, e.g., three times a day, particularly before a carbohydrate-rich meal.

The hypoglycemic effective amount of active ingredient employed in the treatment of diabetes may vary depending on the particular compound employed, the mode of administration and the severity of the condition being treated. However, in general, satisfactory results in the treatment of diabetes are obtained when a compound of formula (I), or a pharmaceutically acceptable salt thereof, is administered at a daily dosage of from about 0.5 milligrams to about 200 milligrams per kilogram of animal body weight, preferably given orally and in divided doses two to four times a day, or in sustained release form. For most large animals, the total daily dosage is from about 25 milligrams to about 800 milligrams. Unit dosage forms suitable for internal use comprise from about 6 milligrams to about 400 milligrams of the active compund in intimate admixture with a solid or liquid, pharmaceutically acceptable carrier.

The compounds of formula (I) may be similarly administered in the form of their non-toxic pharmaceutically acceptable acid addition or basic salts. Such salts possess the same order of activity as the free base and are readily prepared by reacting the compound with a pharmaceutically acceptable acid by conventional techniques, and accordingly are included within the scope of this invention. Representative of the inorganic salts are the hydrochloride, hydrobromide, hydroiodide, phosphate (including hydrogen phosphate), metaphosphate, and sulfate (including hydrogen sulfate). Representative examples of the organic salts are the acetate, maleate, fumarate and the like. Examples of the basic salts are the alkali metal salts.

Tablets and capsules containing the ingredients indicated below may be prepared by conventional techniques are are useful in treating diabetes, at a dose of one tablet or capsule, 2 to 4 times a day.

| Ingredients | Weight (mg.) tablet | capsule |
|---|---|---|
| 2-(3-ethyl-5-methyl-4-isoxazolyl)-3-(dimethylaminopropyl)-indole | 200 | 200 |
| tragacanth | 10 | — |
| lactose | 247.5 | 300 |
| corn starch | 25 | — |
| talcum | 15 | — |
| magnesium stearate | 2.5 | — |
| Total | 500 | 500 |

The daily dosages suitable for any particular compound of formula (I) will, of course, depend on a number of factors including relative potency of activity. The preferred compound of the invention is the above compound, 2-(3-ethyl-5-methyl-4-isoxazolyl)-3-(dimethylaminopropyl)-indole. This compound has, for example, been determined to have an ED50 in the above post-prandial hypoglycemia test of 74 mg./kg. p.o. An indicated daily dosage for this compound in the treatment of diabetes by inhibiting post-prandial hypoglycemia would be from about 100 to 1050 milligrams. The compound has an ED 25 of 17 mg/kg p.o. in the fasting hypoglycemia test vs. 200 mg/kg p.o. for the standard tolbutamide. An indicated daily dosage for this compound in the treatment of diabetes as a hypoglycemic agent is from about 25 to 300 milligrams, preferably about 100 to 200 milligrams.

EXAMPLE 1

1-(5-methyl-3-phenyl-4-isoxazolyl)-1-ethanone phenyl hydrazone

A mixture of 80.4 g (0.4 mole) of 4-acetyl-5-methyl-3-phenylisoxazole, 39.4 ml (0.4 mole) of phenyl hydrazine and 500 mg toluenesulfonic acid in 400 ml ethanol is stirred at room temperature for 48 hours. The resulting solid is filtered and washed with cold ether to give 1-(5-methyl-3-phenyl-4-isoxazolyl)-1-ethanol phenyl hydrazone m.p. 129° to 133° C.

Following the above procedure and using in place of 4-acetyl-5-methyl-3-phenylisoxazole an equivalent amount of
(a) 4-acetyl-3-ethyl-5-methyl-isoxazole, or
(b) 4-acetyl-3,5-dimethyl-isoxazole there is obtained
(c) 1-(3-ethyl-5-methyl-4-isoxazolyl)-1-ethanone phenyl hydrazone, or
(d) 1-(3,5-dimethyl-4-isoxazolyl)-1-ethanone phenyl hydrazone respectively.

Again, following the above procedure and using in place of phenyl hydrazine an equivalent amount of
(c) p-fluorophenyl hydrazine there is obtained
(c) 1-(5-methyl-3-phenyl-4-isoxazolyl)-1-ethanone-p-fluorophenyl hydrazone.

EXAMPLE 2

2-(5-methyl-3-phenyl-4-isoxazoly)-indole

To 1350 grams of polyphosphoric acid at 100° to 110° C., there is added portionwise 89.3 g (0.307 mole) of 1-(5-methyl-3-phenyl-4-isoxazolyl)-1-ethanone phenyl hydrazone, while maintaining the temperature between 105° and 115° C. After addition is complete the mixture is stirred at 100° to 110° C. for 3 hours. The mixture is then poured onto ice and water and the resulting solid is filtered and washed with water. The solid is then dissolved in ether, washed with water, dried and evaporated partially and cooled in ice. The resulting solid is filtered and washed with cold ether to give 2-(5-methyl-3-phenyl-4-isoxazolyl)-indole; m.p. 145° to 146° C.

Following the above procedure and using in place of 1-(5-methyl-3-phenyl-4-isoxazolyl)-1-ethanone phenyl hydrazone an equivalent amount of
(a) 1-(3-ethyl-5-methyl-4-isoxazolyl)-1-ethanone phenyl hydrazone,
(b) 1-(3,5-dimethyl-4-isoxazolyl)-1-ethanone phenyl hydrazone, or
(c) 1-(5-methyl-3-phenyl-4-isoxazolyl)-1-ethanone-p-fluorophenyl hydrazone there is obtained
(a) 2-(3-ethyl-5-methyl-4-isoxazolyl)-indole, (b) 2-(3,5-dimethyl-4-isoxazolyl)-indole, or
(c) 5-fluoro-2-(5-methyl-3-phenyl-4-isoxazolyl)-indole respectively.

EXAMPLE 3

2-(5-methyl-3-phenyl-4-isoxazolyl)-3-(dimethylaminomethyl)-indole

A mixture of 20.6 ml. (0.24 mole) 37% aqueous formaldehyde, 18 ml. (0.12 mole) 40% aqueous dimethylamine and 80 ml. acetic acid is cooled to 0° and treated by dropwise addition with 25.5 g. (0.113 mole) 2-(5-methyl-3-phenyl-4-isoxazolyl)-indole in a solution of 45 ml. acetic acid and 125 ml. dioxane. After addition is complete the mixture is stirred for 1 hour at room temperature and poured onto 500 ml. ice-water. The resulting solution is made basic with 20% potassium hydroxide and then extracted with methylene chloride. The methylene chloride is washed with water, brine, dried over anhydrous magnesium sulfate, filtered and evaporated to give 2-(5-methyl-3-phenyl-4-isoxazolyl)-3-(dimethylaminomethyl)-indole.

Following the above procedure and using in place of 2-(5-methyl-3-phenyl-4-isoxazolyl)-indole an equivalent amount of
(a) 2-(3-ethyl-5-methyl-4-isoxazolyl)-indole,
(b) 2-(3,5-dimethyl-4-isoxazolyl)-indole, or
(c) 5-fluoro-2-(5-methyl-3-phenyl-4-isoxazolyl)-indole there is obtained
(a) 2-(3-ethyl-5-methyl-4-isoxazolyl)-3-(dimethylaminomethyl)-indole,
(b) 2-(3,5-dimethyl-4-isoxazolyl)-3-(dimethylaminomethyl)-indole, or
(c) 5-fluoro-2-(5-methyl-3-phenyl-4-isoxazolyl)-3-(dimethylaminomethyl)-indole respectively.

EXAMPLE 4

[[2-(5-methyl-3-phenyl-4-isoxazolyl)-1H-indol-3-yl]methyl]propanedioic acid, diethylester A mixture of 19.8 g (0.06 mole) of 2-(5-methyl-3-phenyl-4-isoxazolyl)-3-(dimethylaminomethyl)-indole and 30 g (0.185 mole) of diethylmalonate is heated to 120° C. and 100 mg of metallic sodium is added. The mixture is then heated for five hours at 120° C. and an additional 100 mg. of metallic sodium is added. The temperature is increased to 140° and maintained for 18 hours. The mixture is cooled and poured into 150 ml 10% hydrochloric acid and extracted with ether. The ether extracts are washed with saturated sodium bicarbonate, dried over anhydrous magnesium sulfate, filtered and evaporated to remove the ether and excess diethylmalonate to give [[2-(5-methyl-3-phenyl-4-isoxazolyl)-1H-indol-3-yl]methyl]propanedioic acid, diethylester as an oil.

Following the above procedure and using in place of 2-(5-methyl-3-phenyl-4-isoxazolyl)-3-(dimethylaminomethyl)-indole an equivalent amount of
(a) 2(3-ethyl-5-methyl-4-isoxazolyl)-3-(dimethylaminomethyl)-indole,
(b) 2-(3,5-dimethyl-4-isoxazolyl)-3-(dimethylaminomethyl)-indole, or
(c) 5-fluoro-2-(5-methyl-3-phenyl-4-isoxazolyl)-3-(dimethylaminomethyl)-indole there is obtained
(a) [[2-(3-ethyl-5-methyl-4-isoxazolyl)-1H-indol-3-yl]methyl]propanedioic acid, diethyl ester,
(b) [[2-(3,5-dimethyl-4-isoxazolyl)-1H-indol-3-yl]methyl]propanedioic acid, diethyl ester, or
(c) [[5-fluoro-2-(5-methyl-3-phenyl-4-isoxazolyl)-1H-indol-3-yl]methyl]propanedioic acid, diethyl ester respectively.

EXAMPLE 5

2-(5-methyl-3-phenyl-4-isoxazolyl)-3-indole propionic acid

A mixture of 22.8 g (0.05 mole) of [[2-(5-methyl-3-phenyl-4-isoxazolyl)-1H-indol-3-yl]methyl]propanedioic acid, diethyl ester and 150 ml of 12N hydrochloric acid is refluxed for 65 hours. The mixture is cooled and extracted with ether. The ether is washed with water, dried over anhydrous magnesium sulfate, filtered and evaporated. The solid residue is then decolorized with charcoal and recrystallized from ether hexane to give 2-(5-methyl-3-phenyl-4-isoxazolyl)-3-indole propionic acid m.p. 170° to 172° C.

Following the above procedure and using in place of [[2-(5-methyl-3-phenyl-4-isoxazolyl)-1H-indol-3-yl]methyl]propanedioic acid, diethyl ester an equivalent amount of
(a) [[2-(3-ethyl-5-methyl-4-isoxazolyl)-1H-indol-3-yl]methyl]propanedioic acid, diethyl ester,
(b) [[2-(3,5-dimethyl-4-isoxazolyl)-1H-indol-3-yl]methyl]propaneioic acid, diethyl ester, or
(c) [[5-fluoro-2-(5-methyl-3-phenyl-4-isoxazolyl)-1H-indol-3-yl]methyl]propanedioic acid, diethyl ester there is obtained
(a) 2-(3-ethyl-5-methyl-4-isoxazolyl)-3-indole propionic acid,
(b) 2-(3,5-dimethyl-4-isoxazolyl)-3-indole propionic acid, or
(c) 5-fluoro-2-(5-methyl-3-phenyl-4-isoxazolyl)-3-indole propionic acid respectively.

EXAMPLE 6

2-(5-methyl-3-phenyl-4-isoxazolyl)-3-indole propionyl chloride

A mixture of 5.1 g (0.0147 mole) of 2-(5-methyl-3-phenyl-4-isoxazolyl)-3-indole propionic acid and 7.0 g (0.059 mole) of thionyl chloride in 200 ml tetrahydrofuran is stirred for 18 hours at room temperature. The solvent is then removed in vacuo to give 2-(5-methyl-3-phenyl-4-isoxazolyl)-3-indole propionyl chloride.

Following the above procedure and using in place of 2-(5-methyl-3-phenyl-4-isoxazolyl)-3-indole propionic acid an equivalent amount of
(a) 2-(3-ethyl-5-methyl-4-isoxazolyl)-3-indole propionic acid,
(b) 2-(3,5-dimethyl-4-isoxazolyl)-3-indole propionic acid, or
(c) 5-fluoro-2-(5-methyl-3-phenyl-4-isoxazolyl)-3-indole propionic acid there is obtained
(a) 2-(3-ethyl-5-methyl-4-isoxazolyl)-3-indole propionyl chloride
(b) 2-(3,5-dimethyl-4-isoxazolyl)-3-indole propionyl chloride, or
(c) 5-fluoro-2-(5-methyl-3-phenyl-4-isoxazolyl)-3-indole propionyl chloride respectively.

EXAMPLE 7

N,N-dimethyl-2-(5-methyl-3-phenyl-4-isoxazolyl)-3-indolepropionamide

A suspension of 5.35 g (0.0147 mole) of 2-(5-methyl-3-phenyl-4-isozazolyl)-3-indole propionyl chloride in 100 ml methylene chloride is added to 150 ml 40% aqueous dimethylamine while maintaining temperatures at 0° to 10° C. The mixture is then stirred for two hours at room temperature and then extracted with methylene chloride. The combined organic layers are washed with water, dried over magnesium sulfate, filtered and evaporated. The solid residue is recrystallized from ethanol to give N,N-dimethyl-2-(5-methyl-3-phenyl-4-isoxazolyl)-3-indolepropionamide m.p. 174° to 177° C.

Following the above procedure and using in place of 2-(5-methyl-3-phenyl-4-isoxazolyl)-3-indole propionyl chloride an equivalent amount of (a) 2-(3-ethyl-5-methyl-4-isoxazolyl)-3-indole propionyl chloride,
(b) 2-(3,5-dimethyl-4-isoxazolyl)-3-indole propionyl chloride, or
(c) 5-fluoro-2-(5-methyl-3-phenyl-4-isoxazolyl)-3-indole prioionyl chloride there is obtained (a) N,N-dimethyl-2-(3-ethyl-5-methyl-4-isoxazolyl)-3-indolepropionamide,
(b) N,N-dimethyl-2-(3,5-dimethyl-4-isoxazolyl)-3-indolepropionamide, or
(c) 5-fluoro-N,N-dimethyl-2-(5-methyl-3-phenyl-4-isoxazolyl)-3-indole propionamide respectively.

Again following the above procedure and using in place of dimethylamine an equivalent amount of
(d) morpholine
(e) pyrrolidine, or
(f) piperidine there is obtained (d) 4-[3-[2-(5-methyl-3-phenyl-4-isoxazolyl)-1H-3-indolyl]propionyl]morpholine,
(e) 1-[3-[2-(5-methyl-3-phenyl-4-isoxazolyl)-1H-3-indolyl]propionyl]pyrrolidine, or
(f) 1-[3-[2-(5-methyl-3-phenyl-4-isoxazolyl)-1H-3-indolyl]propionyl]piperidine.

Also, following the above procedure and using in place of 2-(5-methyl-3-phenyl-4-isoxazolyl)-3-indole propionyl chloride an equivalent amount of 2-(3-ethyl-5-methyl-4-isoxazolyl)-3-indole propionyl chloride and using in place of dimethylamine an equivalent amount of pyrrolidine there is obtained
(g) 1-[3-[2-(3-ethyl-5-methyl-4-isoxazolyl)-1H-3-indolyl]propionyl]pyrrolidine.

EXAMPLE 8

2-(5-methyl-3-phenyl-4-isoxazolyl)-3-(3-dimethylaminopropyl)-indole

A solution of 2.0 g (0.0054 mole) of N,N-dimethyl-2-(5-methyl-3-phenyl-4-isoxazolyl)-3-indole propionamide in 80 ml tetrahydrofuran is added to a suspension of 0.82 g (0.0216 mole) of lithium aluminum hydride in 40 ml tetrahydrofuran dropwise, maintaining the temperature between 20° and 25° C. After the addition is complete the mixture is stirred at room temperature for two hours, cooled and quenched by the addition of 2 ml of water in 20 ml tetrahydrofuran. The resulting mixture is dried over magnesium sulfate, filtered and evaporated. The solid residue is recrystallized from ethanol to give 2-(5-methyl-3-phenyl-4-isoxazolyl)-3-(3-dimethylaminopropyl)-indole m.p. 156° to 157° C.

Following the above procedure and using in place of N,N-dimethyl-2-(5methyl-3-phenyl-4-isoxazolyl)-3-indole propionamide an equivalent amount of (a) N,N-dimethyl-2-(3-ethyl-5-methyl-4-isoxazolyl)-3-indole propionamide,
(b) N,N-dimethyl-2-(3,5-dimethyl-4-isozazolyl)-3-indole propionamide,
(c) 5-fluoro-N,N-dimethyl-2-(5-methyl-3-phenyl-4-isoxazolyl)-3-indole propionamide,
(d) 4-[3-[2-(5-methyl-3-phenyl-4-isoxazolyl)-1H-3-indolyl]propionyl]morpholine,
(e) 1-[3-[2-(5-methyl-3-phenyl-4-isoxazolyl)-1H-3-indolyl]propionyl]pyrrolidine,
(f) 1-[3-[2-(5-methyl-3-phenyl-4-isoxazolyl)-1H-3-indolyl]propionyl]piperidine, or
(g) 1-[3-[2-(3-ethyl-5-methyl-4-isoxazolyl)-1H-3-indolyl]propionyl]pyrrolidine there is obtained (a) 2-(3-ethyl-5-methyl-4-isoxazolyl)-3-(3-dimethylaminopropyl)-indole,
(b) 2-(3,5-dimethyl-4-isoxazolyl)-3-(3-dimethylaminopropyl)-indole,
(c) 5-fluoro-2-(5-methyl-3-phenyl-4-isoxazolyl)-3-(3-dimethylaminopropyl)-indole,
(d) 2-(5-methyl-3-phenyl-4-isoxazolyl)-3-(3-morpholinopropyl)-indole,
(e) 2-(5-methyl-3-phenyl-4-isoxazolyl)-3-(3-pyrrolidinopropyl)-indole,
(f) 2-(5-methyl-3-phenyl-4-isoxazolyl)-3-(3-piperidinopropyl)-indole, or
(g) 2-(3-ethyl-5-methyl-4-isoxazolyl)-3-(3-pyrrolidinopropyl)-indole respectively.

The title compound of Example 8 has an $ED_{50}$ of 106 mg/kg p.o. in rats in the treatment of diabetes in particular the inhibition of post-prandial hyperglycemia.

EXAMPLE 9

2-(3-ethyl-5-methyl-4-isoxazolyl)-3-acetyl indole

To a mixture of 0.77 milliliters (13.45 m mole) of acetic acid and 0.17 grams (1.47 m mole) of 85% phosphoric acid in 10 milliliters of acetonitrile is added, at room temperature, 1.9 milliliters (13.45 m mole) of trifluoroacetic acid anhydride. The mixture is stirred for 15 minutes and then treated by dropwise addition with 1.0 grams (4.42 m mole) of 2-(3-ethyl-5-methyl-4-isoxazolyl)-indole in 10 milliliters acetonitrile. The mixture is stirred for 3½ hours at room temperature and then poured onto water and extracted with ether. The ether extracts are dried over magnesium sulfate, filtered and evaporated in vacuo. The resulting oil is filtered through silica gel using 10% methanol/methylene chloride. The solvent is evaporated, and the oil obtained is dissolved in ether. The solution is washed with 10% sodium bicarbonate solution, decolorized with charcoal, dried over magnesium sulfate and evaporated in vacuo. The resulting oil crystallizes upon treatment with ether to give 3-acetyl-2-(3-ethyl-5-methyl-4-isoxazolyl)-indole, m.p. 170°-171°.

In the alternate procedure, 41.8 grams (0.163 moles) of silver trifluoromethanesulfonate is added portionwise to a solution of 33.5 grams (0.148 mole) of 2-(3-ethyl-5-methyl-4-isoxazolyl)-indole in 450 milliliters of methylene chloride. The resulting suspension is then treated by dropwise addition with 12.8 grams (0.163 moles) of acetyl chloride in 50 milliliters of methylene chloride. The temperature rises to 35° C. during the addition. After the addition is complete the mixture is stirred at room temperature for 4 hours and then filtered. The filtrate is washed with 150 milliliters of of 2N sodium hydroxide, water and 2N sodium hydroxide, then dried over anhydrous magnesium sulfate and finally evaporated in vacuo to yield an oil. The oil is crystallized from ether to give 2-(3-ethyl-5-methyl-4-isoxazolyl)-3-acetyl indole, m.p. 170°-173° C.

Following the above procedures and using in place of 2-(3-ethyl-5-methyl-4-isoxazolyl)indole an equivalent amount of
(a) 2-(5-methyl-3-phenyl-4-isoxazolyl)-indole, or
(b) 2-(3,5-dimethyl-4-isoxazolyl)-indole there is obtained
(a) 2-(5-methyl-3-phenyl-4-isoxazolyl)-3-acetyl indole, or
(b) 2-(3,5-dimethyl-4-isoxazolyl)-3-acetyl indole, respectively.

EXAMPLE 10

3-dimethylamino-1-[2-(3-ethyl-5-methyl-4-isoxazolyl)-1H-indol-3-yl]-1-propanone [Compounds II]

A mixture of 12 g. (0.045 mole) of 2-(3-ethyl-5-methyl-4-isoxazolyl)-3-acetyl indole, 4 g. (0.049 mole) of dimethylamine hydrochloride, and 0.5 ml. concentrated hydrochloric acid in 70 ml. of ethanol is heated to reflux and treated by portionwise addition with 14 g. (0.470 mole) of paraformaldehyde over 5 hours. The resulting mixture is refluxed an additional 24 hours, cooled and evaporated in vacuo. The residue is then dissolved in 300 ml. methylene chloride and washed with 200 ml. 2N hydrochloric acid. The aqueous acid is cooled and made basic with 2N sodium hydroxide and extracted with methylene chloride. The organic layer is dried over anhydrous magnesium sulfate, filtered and evaporated in vacuo. The residue is crystallized from ether to give 3-dimethylamino-1-[2-(3-ethyl-5-methyl-4-isoxazolyl)-1H-indole-3-yl]-1-propanone, m.p. 146°–148° C.

Following the above procedure and using in place of 2-(3-ethyl-5-methyl-4-isoxazolyl)-3-acetyl indole an equivalent amount of
(a) 2-(5-methyl-3-phenyl-4-isoxazolyl)-3-acetylindole, or
(b) 2-(3,5-dimethyl-4-isoxazolyl)-3-acetyl indole there is obtained
(a) 3-dimethylamino-1-[2-5-methyl-3-phenyl-4-isoxazolyl-1H-indol-3-yl]-1-propanone, or
(b) 3-dimethylamino-1-[2-(3,5-dimethyl-4-isoxazolyl)-1H-indol-3-yl]-1-propanone, respectively.

Again following the above procedure and using in place of dimethylamine an equivalent amount of
(c) pyrrolidine there is obtained
(c) 3-pyrrolidinino-1-[2-(3-ethyl-5-methyl-4-isoxazolyl)-1H-indol-3-yl]-1-propanone.

EXAMPLE 11

2-(3-ethyl-5-methyl-4-isoxazolyl)-3-(3-dimethylaminopropyl)-indole [Compounds I]

A mixture of 5.0 grams (0.015 mole) of 3-dimethylamino-1-[2-(3-ethyl-5-methyl-4-isoxazolyl)-2H-indol-3-yl]-1-propanone in 120 milliliters of tetrahydrofuran is added dropwise to a refluxing mixture of 2.0 grams of lithium aluminum hydride (0.053 mole) and 200 milliliters of tetrahydrofuran. The combined mixture is refluxed for one hour, cooled in an ice bath and quenched by the cautious addition of 7 milliliters of water. The mixture is then filtered through celite and the solvent evaporated in vacuo to yield an oil, which slowly crystallized. The crystals are triturated with ether to give 2-(3-ethyl-5-methyl-4-isoxazolo)-3-(3-dimethylaminopropyl)-indole, m.p. 131°–133° C.

Following the above procedure and using in place of 3-dimethylamino-1-[2-(3-ethyl-5-methyl-4-isoxazolyl)-1H-indol-3-yl]-1-propanone an equivalent amount of
(a) 3-dimethylamino-1-[2-(5-methyl-3-phenyl-4-isoxazolyl)-1H-indol-3-yl]-1-propanone,
(b) 3-dimethylamino-1-[2-(3,5-dimethyl-4-isoxazolyl)-1H-indol-3-yl]-1-propanone, or
(c) 3-pyrrolidino-1-[2-(3-ethyl-5-methyl-4-isoxazolyl)-1H-indol-3-yl]-1-propanone there is obtained
(a) 2-(5-methyl-3-phenyl-4-isoxazolyl)-3-(3-dimethylaminopropyl)-indole,
(b) 2-(3,5-dimethyl-4-isoxazolyl)-3-(3-dimethylaminopropyl)-indole, or
(c) 2-(3-ethyl-5-methyl-4-isoxazolyl)-3-(3-pyrrolidinopropyl)-indole, respectively.

EXAMPLE 12

2-(3-ethyl-5-methyl-4-isoxazolyl)-3-(4-dimethylaminobutyl)-indole

Step A 2-(3-ethyl-5-methyl-4-isoxazolyl)-γ-oxo-indole-3-butanoic acid, methyl ester A solution of 59.4 grams (0.45 mole) of mono-methyl succinate in 300 ml acetonitrile is treated by dropwise addition with 5.5 grams of 85% phosphoric acid and then by dropwise addition with 63.5 ml (0.45 mole) of trifluoroacetic acid anhydride. The mixture is stirred 15 minutes at room temperature and then treated by dropwise addition with 33.9 grams (0.15 mole) of 2-(3-ethyl-5-methyl-4-isoxazolyl)-indole in 300 ml of acetonitrile. The mixture is stirred at room temperature overnight, after which 1.5 liters of water and 1 liter of ether are added. The two layers are separated, and the ether is washed with water and made basic by the addition of solid sodium carbonate and water. The mixture is stirred 1 hour at room temperature, following which the layers are separated. The ether layer is then washed with water, dried over MgSO$_4$, filtered and evaporated to give the title compound.

Step B 2-(3-ethyl-5-methyl-4-isoxazolyl)-γ-oxo-indole-3-butanoic acid

A solution of the above 2-(3-ethyl-5-methyl-4-isoxazolyl)-γ-oxo-indole-3-butanoic acid, methyl ester in 250 ml methanol is treated with 250 ml of 2N sodium hydroxide solution; and the mixture is heated 15 minutes to 40°–45° and then stirred at room temperature for 1 hour. Ether and water are added to the mixture and the layers then separated. The ether layer is washed with water; after which the combined aqueous layers are washed with ether, treated with charcoal and filtered through celite. The aqueous basic solution is made acidic by careful addition of concentrated HCl and extracted with ether. The ether solution is then washed with water, brine, dried over MgSO$_4$, filtered and evaporated. The resulting foam is crystallized to give the title compound, m.p. 98°–110° C.

Step C 2-(3-ethyl-5-methyl-4-isoxazoly)-N,N-dimethyl-γ-oxo-indole-3-butanamide A solution of 978 mg (0.003 mole) of 2-(3-ethyl-5-methyl-4-isoxazolyl)-γ-oxo-indole-3-butanoic acid in 15 ml of methylene chloride is treated with 345 mg (0.003 mole) of N-hydroxy-succinimide followed by the dropwise addition of 618 mg (0.003 mole) of dicyclohexyl-carbodiimide in 10 ml CH$_2$Cl$_2$. The resulting mixture is stirred 5 hours at room temperature. The mixture is then filtered, and the filter cake is washed with CH$_2$Cl$_2$. The combined CH₂Cl₂ layers are added dropwise to 20 ml of 40% aqueous dimethylamine and 20 ml of CH₂Cl₂. The mixture is stirred overnight; following which water is added and the layers separated. The CH₂Cl₂ layer is washed with water, brine, dried over MgSO₄, filtered and evaporated. The residue is crystallized to give the title compound, m.p. 144.5°–148° C.

Step D
2-(3-ethyl-5-methyl-4-isoxazolyl)-3-(4-dimethylaminobutyl)-indole

A solution of 5.3 grams (0.015 mole) of 2-(3-ethyl-5-methyl-4-isoxazolyl)-N,N-dimethyl-   -oxo-indole-3-butanamide in 75 ml dry THF is added dropwise to a refluxing suspension of 1.71 grams (0.045 mole) of LiAlH₄ and 50 ml THF. The mixture is refluxed 2 hours after addition and then cooled and quenched by the addition of ethyl acetate, 2N sodium hydroxide and water. The mixture is filtered and the THF evaporated. The residue is dissolved in CH₂Cl₂, washed with water, dried over MgSO₄, filtered and evaporated. The residue is dissolved in ether and converted to the hydrochloride salt with gaseous HCl giving the title compound as the hydrochloride, m.p. 155.5°–157.5° C.

What is claimed is:

1. A compound of the formula

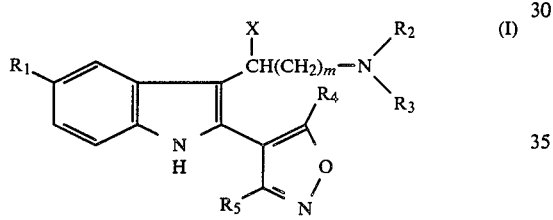

where
m is 2, 3, or 4,
X is hydrogen or hydroxy,
R₁ represents hydrogen, fluoro, chloro, lower alkyl having 1 to 4 carbon atoms, or lower alkoxy having 1 to 4 carbon atoms, and
R₂ and R₃ each independently represent lower alkyl having 1 to 4 carbon atoms, or
R₂ and R₃ together with N represent

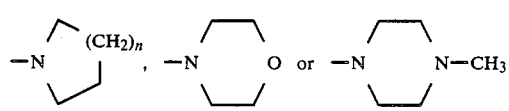

wherein
n is 1, 2 or 3, and
R₄ represents hydrogen or lower alkyl having 1 to 4 carbon atoms, and
R₅ represents hydrogen, lower alkyl, phenyl or phenyl substituted with fluoro, chloro, lower alkyl having 1 to 4 carbon atoms or lower alkoxy having 1 to 4 carbon atoms
with the proviso that when X is hydroxy, m is 3 or 4, or a pharmaceutically acceptable acid addition salt thereof.

2. A compound of the formula

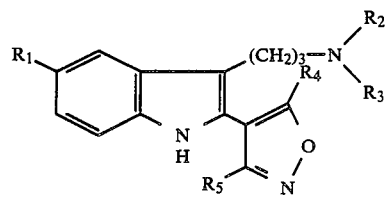

wherein
R₁ represents hydrogen, fluoro, chloro, lower alkyl having 1 to 4 carbon atoms, or lower alkoxy having 1 to 4 carbon atoms, and
R₂ and R₃ each independently represent lower alkyl having 1 to 4 carbon atoms, or
R₂ and R₃ together with N represent

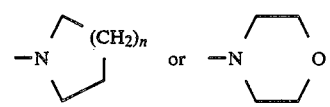

wherein
n is 1, 2 or 3, and
R₄ represents hydrogen or lower alkyl having 1 to 4 carbon atoms, and
R₅ represents hydrogen, lower alkyl or unsubstituted phenyl or a pharmaceutically acceptable acid addition salt thereof.

3. A compound of the formula

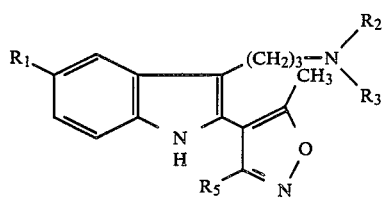

wherein R₁, R₂, R₃ and R₅ are as defined in claim 2 or a pharmaceutically acceptable acid addition salt thereof.

4. The compound of claim 2 wherein R₅ is ethyl.

5. The compound of claim 2 wherein R₅ is unsubstituted phenyl.

6. The compound of claim 2 which is 2-(5-methyl-3-phenyl-4-isoxazolyl)-3-(3-dimethylaminopropyl)-indole or a pharmaceutically acceptable acid addition salt thereof.

7. The compound of claim 2 which is 2-(3-ethyl-5-methyl-4-isoxazolyl)-3-(3-dimethylaminopropyl)-indole or a pharmaceutically acceptable acid addition salt thereof.

8. The compound of claim 2 which is 2-(5-methyl-3-phenyl-4-isoxazolyl)-3-(3-pyrrolidinopropyl)-indole or a pharmaceutically acceptable acid addition salt thereof.

9. The compound of claim 1 which is 2-(3-ethyl-5-methyl-4-isoxazolyl)-3-(4-dimethylaminobutyl)-indole or a pharmaceutically acceptable acid addition salt thereof.

10. A compound of the formula

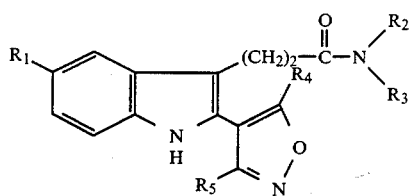

wherein $R_1$, $R_2$, $R_3$, $R_4$ and $R_5$ are as defined in claim 1 or a pharmaceutically acceptable acid addition salt thereof.

11. A compound of the formula

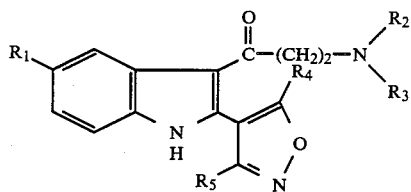

where $R_5$ is phenyl, and $R_1$, $R_2$, $R_3$ and $R_4$ are as defined in claim 1 or a pharmaceutically acceptable acid addition salt thereof.

12. A compound of the formula

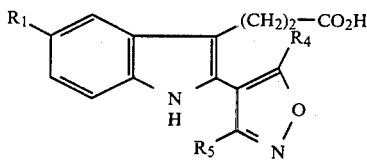

where $R_1$, $R_4$ and $R_5$ are as defined in claim 1.

13. A method of treating diabetes by inhibiting postprandial hyperglycemia which comprises administering to an animal in need of said treatment an effective amount of a compound of claim 1.

14. A pharmaceutical composition comprising a compound of claim 1 and a pharmaceutically acceptable diluent or carrier therefor.

15. A method for treating diabetes which comprises administering to an animal in need of said treatment a hypoglycemic effective amount of a compound of claim 1.

16. The compounds of claim 1 in which m is 3 or 4, X is hydrogen or hydroxy and $R_1$, $R_2$, $R_3$, $R_4$ and $R_5$ are as defined in claim 1.

17. The compound of claim 10 which is N,N-dimethyl-2-(5-methyl-3-phenyl-4-isoxazolyl)-3-indole-propionamide.

18. The compound of claim 10 which is N-N-dimethyl-2-(3-ethyl-5-methyl-4-isoxazolyl)-3-indole-propionamide.

19. The compound of claim 12, which is 2-(5-methyl-3-phenyl-4-isoxazolyl)-3-indole propionic acid.

20. The compound of claim 12, which is 2-(3-ethyl-5-methyl-4-isoxazolyl)-3-indole propionic acid.

* * * * *